(12) United States Patent
LaFleur et al.

(10) Patent No.: US 11,883,476 B2
(45) Date of Patent: Jan. 30, 2024

(54) CANINE LYME DISEASE VACCINE

(71) Applicant: Intervet Inc., Madison, NJ (US)

(72) Inventors: Rhonda LaFleur, Omaha, NE (US);
Jennifer C. Dant, Elkhorn, NE (US);
Mark A. Mogler, Ames, IA (US);
Steven M. Callister, Onalaska, WI (US); Zhichang Xu, Omaha, NE (US)

(73) Assignee: Intervet Inc., Rahway, NJ (US)

( * ) Notice: Subject to any disclaimer, the term of this patent is extended or adjusted under 35 U.S.C. 154(b) by 170 days.

(21) Appl. No.: 16/767,715

(22) PCT Filed: Dec. 3, 2018

(86) PCT No.: PCT/EP2018/083306
§ 371 (c)(1),
(2) Date: May 28, 2020

(87) PCT Pub. No.: WO2019/110486
PCT Pub. Date: Jun. 13, 2019

(65) Prior Publication Data
US 2020/0289634 A1 Sep. 17, 2020

Related U.S. Application Data

(60) Provisional application No. 62/594,342, filed on Dec. 4, 2017.

(51) Int. Cl.
| A61K 39/02 | (2006.01) |
| A61P 31/04 | (2006.01) |
| A61K 39/193 | (2006.01) |
| A61K 39/00 | (2006.01) |

(52) U.S. Cl.
CPC ...... *A61K 39/0225* (2013.01); *A61K 39/0241* (2013.01); *A61K 39/193* (2013.01); *A61P 31/04* (2018.01); *A61K 2039/53* (2013.01); *A61K 2039/545* (2013.01); *A61K 2039/552* (2013.01)

(58) Field of Classification Search
CPC ............ A61K 39/0225; A61K 39/0241; A61K 39/193; A61K 2039/53; A61K 2039/545; A61K 2039/552; A61P 31/04
See application file for complete search history.

(56) References Cited

U.S. PATENT DOCUMENTS

| 6,210,676 B1 | 4/2001 | Callister et al. | |
| 6,316,005 B1 | 11/2001 | Korshus et al. | |
| 6,451,769 B1* | 9/2002 | Huebner | C07K 14/20 977/804 |
| 6,464,985 B1 | 10/2002 | Callister et al. | |
| 6,872,550 B1 | 3/2005 | Livey et al. | |
| 8,137,678 B2 | 3/2012 | Callister et al. | |
| 8,414,901 B2* | 4/2013 | Callister | A61P 31/04 424/234.1 |
| 8,460,913 B2 | 6/2013 | Kamrud et al. | |
| 9,238,065 B2* | 1/2016 | Chu | A61K 39/0241 |
| 9,441,247 B2 | 9/2016 | Rayner et al. | |
| 9,562,079 B2* | 2/2017 | Lohse | C07K 14/20 |
| 10,983,121 B2* | 4/2021 | Callister | G01N 33/569 |
| 2008/0181916 A1* | 7/2008 | Callister | A61P 31/04 424/234.1 |
| 2012/0141530 A1* | 6/2012 | Callister | A61P 31/12 424/234.1 |
| 2012/0142023 A1* | 6/2012 | Ascoli | G01N 33/56911 435/7.5 |
| 2014/0314801 A1* | 10/2014 | Lohse | C07K 14/20 424/190.1 |
| 2016/0083435 A9* | 3/2016 | Lohse | C07K 14/20 424/190.1 |
| 2020/0289634 A1* | 9/2020 | LaFleur | A61P 31/04 |
| 2020/0323975 A1* | 10/2020 | Mogler | A61K 9/12 |

FOREIGN PATENT DOCUMENTS

| CN | 104379164 A | 2/2015 |
| EP | 1939294 A1 | 7/2008 |
| JP | 2015514776 A | 5/2015 |
| WO | 2005007689 A1 | 1/2005 |
| WO | 2007047749 A1 | 4/2007 |
| WO | 2013006834 A1 | 1/2013 |
| WO | 2013116770 A1 | 8/2013 |
| WO | 2013158818 A2 | 10/2013 |
| WO | 2014005958 A1 | 1/2014 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Servin-Blanco (Human Vaccines and Immunotherapeutics vol. 12 No. 10, pp. 2640-2648).*
Baranton, Guy et al., Delineation of Borrelia burgdorferi Sensu Stricto, *Borrelia garinii* sp. nov., and Group VS461 Associated with Lyme Borreliosis, International Journal of Systematic Bacteriology, 1992, 378-383, 42(3).
Barbour, Alan G. et al., Heterogeneity of Major Proteins in Lyme Disease Borreliae: A Molecular Analysis of North American and European Isolates, The Journal of Infectious Diseases, 1985, 478-484, 152(3).
Bredenbeek, Peter J. et al., Sindbis Virus Expression Vectors: Packaging of RNA Replicons by Using Defective Helper RNAs, Journal of Virology, 1993, 6439-6446, 67(11).
Brisson, D et al., Biodiversity of Borrelia burgdorferi Strains in Tissues of Lyme Disease Patients, PloS One, 2011, e22926, pp. 1-5, vol. 6, Issue 8.

(Continued)

*Primary Examiner* — Robert A Zeman
(74) *Attorney, Agent, or Firm* — David J. Kerwick

(57) ABSTRACT

The present invention provides a vaccine for canine Lyme disease and methods of making and using the vaccine alone, or in combinations with other protective agents.

17 Claims, No Drawings
Specification includes a Sequence Listing.

(56) References Cited

OTHER PUBLICATIONS

Buckles, Eric L. et al., Analysis of Antibody Response in Humans to the Type A OspC Loop 5 Domain and Assessment of the Potential Utility of the Loop 5 Epitope in Lyme Disease Vaccine Development, Clinical and Vaccine Immunology, 2006, 1162-1165, 13(10).

Caine, Jennifer A. et al.., A Short-Term Borrelia burgdorferi Infection Model Identifies Tissue Tropisms and Bloodstream Survival Conferred by Adhesion Proteins, Infection and Immunity, 2015, 3184-3194, 83(8).

Callister, Steven M. et al., Detection of Borreliacidal Antibodies by Flow Cytometry, Arch. Intern. Med., 1994, 1625-1632, 154.

Callister, Steven M. et al., Sensitivity and Specificity of the Borreliacidal-Antibody Test during Early Lyme Disease: a "Gold Standard"?, Clinical and Diagnostic Laboratory Immunology, 1996, 399-402, 3(4).

Chu, Hsien-Jue et al., Immunogenicity and efficacy study of a commercial Borrelia burgdorferi bacterin, JAVMA, 1992, 403-411, 201.

Dambach, D.M. et al., Morphologic, Immunohistochemical, and Ultrastructural Characterization of a Distinctive Renal Lesion in Dogs Putatively Associated with Borrelia burgdorf eri Infection: 49 Cases (1987-1992), Vet Pathol, 1997, 85-96, 34.

Earnhart, Christopher G. et al., OspC Phylogenetic Analyses Support the Feasibility of a Broadly Protective Polyvalent Chimeric Lyme Disease Vaccine, Clinical and Vaccine Immunology, 2007, 628-634, 14(5).

Fikrig, Erol et al., Selection of Variant Borrelia burgdorferi Isolates from Mice Immunized with Outer Surface Protein A or B, Infection and Immunity, 1995, 1658-1662, 63(5).

Frolov, Ilya et al., Alphavirus-based expression vectors: Strategies and applications, Proc. Natl. Acad. Sci. USA, 1996, 11371-11377, 93.

Gipson, CL et al., Evaluation of Venezuelan Equine Encephalitis (VEE) replicon-based Outer surface protein A (OspA) vaccines in a tick challenge mouse model of Lyme disease, Vaccine, 2003, 3875-3884, vol. 21, No. 25-26.

Hanincová, Klára et al., Epidemic Spread of Lyme Borreliosis, Northeastern United States, Emerging Infectious Diseases, 2006, 604-610, 12(4).

Heikkilä, Tero et al., Recombinant BBK32 Protein in Serodiagnosis of Early and Late Lyme Borreliosis, Journal of Clinical Microbiology, 2002, 1174-1180, 40(4).

Hovius, Joppe W.R. et al., Antibodies against Specific Proteins of and Immobilizing Activity against Three Strains of Borrelia burgdorferi Sensu Lato Can Be Found in Symptomatic but Not in Infected Asymptomatic Dogs, Journal of Clinical Microbiology, 2000, 2611-2621, 38(7).

Ikushima, Masako et al., Speci¢c immune response to a synthetic peptide derived from outer surface protein C of Borrelia burgdorferi predicts protective borreliacidal antibodies, FEMS Immunology and Medical Microbiology, 2000, 15-21, 29.

International Search Report of PCT/EP2018/083306, dated Feb. 25, 2019, 17 pages.

Jacobson, Richard H. et al., Lyme Disease: Laboratory Diagnosis of Infected and Vaccinated Symptomatic Dogs, Seminars in Veterinary Medicine and Surgery (Small Animal), 1996, 172-182, 11(3).

Jobe, Dean A. et al., Ability of Canine Lyme Disease Vaccine to Protect Hamsters against Infection with Several Isolates of Borrelia burgdorferi, Journal of Clinical Microbiology, 1994, 618-622, 32(3).

Jobe, Dean A. et al., C-Terminal Region of Outer Surface Protein C Binds Borreliacidal Antibodies in Sera from Patients with Lyme Disease, Clinical and Diagnostic Laboratory Immunology, 2003, 573-578, 10(4).

Kamrud, K.I. et al., Development and characterization of promoterless helper RNAs for the production of alphavirus replicon particle, Journal of General Virology, 2010, 1723-1727, 91(Pt 7).

Lafleur, Rhonda L. et al., One-Year Duration of Immunity Induced by Vaccination with a Canine Lyme Disease Bacterin, Clinical and Vaccine Immunology, 2010, 870-874, 17(5).

Lafleur, Rhonda L. et al., Vaccination with the ospA- and ospB-Negative Borrelia burgdorferi Strain 50772 Provides Significant Protection against Canine Lyme Disease, Clinical and Vaccine Immunology, 2015, 836-839, 22(7).

Lafleur, RL et al., Bacterin That Induces Anti-OspA and Anti-OspC Borreliacidal Antibodies Provides a High Level of Protection against Canine Lyme Disease, Clinical and Vaccine Immunology, 2009, 253-259, vol. 16, No. 2.

Lagal, Vanessa et al., Genetic Diversity among Borrelia Strains Determined by Single-Strand Conformation Polymorphism Analysis of the ospC Gene and its Association with Invasiveness, Journal of Clinical Microbiology, 2003, 5059-5065, 41(11).

Lee, John S. et al., Multiagent vaccines vectored by Venezuelan equine encephalitis virus replicon elicits immune responses to Marburg virus and protection against anthrax and botulinum neurotoxin in mice, Vaccine, 2006, 6886-6892, 24.

Liljestrom, P. et al., A new generation of animal cell expression vectors based on the semliki forest virus replicon, Biotechnology, 1991, pp. 1356-1361, 9.

Littman, Meryl P. et al., ACVIM Small Animal Consensus Statement on Lyme Disease in Dogs: Diagnosis, Treatment, and Prevention, J Vet Intern Med, 2006, 422-434, 20.

Lovrich, S.D. et al., Abilities of OspA Proteins from Different Seroprotective Groups of Borrelia burgdorferi to Protect Hamsters from Infection, Infection and Immunity, 1995, 2113-2119, 63(6).

Lovrich, Steven D. et al., Borreliacidal OspC Antibodies Specific for a Highly Conserved Epitope are Immunodominant in Human Lyme Disease and Do Not Occur in Mice or Hamsters, Clinical and Diaganostic Laboratory Immunology, 2005, 746-751, 12(6).

Ma, Jianneng et al., Safety, efficacy, and immunogenicity of a recombinant Osp subunit canine Lyme disease vaccine, Vaccine, 1996, 1366-1374, 14(14).

Ohnishi, Jun et al., Antigenic and genetic heterogeneity of Borrelia burgdorferi populations transmitted by ticks, Proc. Natl. Acad. Sci. USA, 2001, 670-675, 98(2).

Ornstein, Katharina et al., Characterization of Lyme Borreliosis Isolates from Patients with Erythema Migrans and Neuroborreliosis in Southern Sweden, Journal of Clinical Microbiology, 2001, 1294-1298, 39(4).

Pal, Utpal et al., Attachment of Borrelia burgdorferi within Ixodes scapularis mediated by outer surface protein A, Journal of Clinical Investigation, 2000, 561-569, 106.

Pushko, Peter et al., Replicon-Helper Systems from Attenuated Venezuelan Equine Encephalitis Virus: Expression of Heterologous Genes in Vitro and Immunization against Heterologous Pathogens in Vivo, Virology, 1997, 389-401, 239.

Rhodes, D.V.L. et al., Identification of Borrelia burgdorferi ospC genotypes in canine tissue following tick Infestation: Implications for Lyme disease vaccine and diagnostic assay design, Vet. J., 2013, 1-15, 198(2).

Rousselle, Jill C. et al., Borreliacidal Antibody Production against Outer Surface Protein C of Borrelia burgdorferi, J. Infect. Dis., 1998, 733-741, 178.

Schwan, T.G., Temporal regulation of outer surface proteins of the Lyme-disease spirochaete Borrelia burgdorferi, Biochemical Society Transactions, 2003, 108-112, 31(1).

Schwan, Tom G. et al., Induction of an outer surface protein on Borrelia burgdorferi during tick feeding, Proc. Natl. Acad. Sci. USA, 1995, 2909-2913, 92.

Straubinger, Reinhard K. et al., Protection against tick-transmitted Lyme disease in dogs vaccinated with a multiantigenic vaccine, Vaccine, 2002, 181-193, 20.

Summers, B. A. et al., Histopathological Studies of Experimental Lyme Disease in the Dog, J. Comp. Path., 2005, 1-13, 133.

Tokarz, Rafal et al., Combined Effects of Blood and Temperature Shift on Borrelia burgdorferi Gene Expression as Determined by Whole Genome DNA Array, Infection and Immunity, 2004, 5419-5432, 72(9).

Vander Veen, RL et al., Alphavirus replicon vaccines, Animal Health Research Reviews, 2012, 1-9, vol. 13, No. 1.

(56) References Cited

OTHER PUBLICATIONS

Wang, Ing-Nang et al., Genetic Diversity of ospC in a Local Population of Borrelia burgdorferi sensu stricto, Genetics, 1999, 15-30, 151.

Wikle, R.E.et al., Canine Lyme Disease: One-Year Duration of Immunity Elicited With a Canine OspA Monovalent Lyme Vaccine, Intern J Appl Res Vet Med, 2006, 23-28, 4(1).

Day, M.J. et al., Guidelines for the Vaccination of Dogs and Cats, Vaccination Guidelines Group (VGG) of the World Small Animal Veterinary Association (WSAVA), 2016, 1-11, 57.

Day, M.J. et al., Guidelines for the Vaccination of Dogs and Cats, Vaccination Guidelines Group (VGG) of the World Small Animal Veterinary Association (WSAVA), 2016, 1-14, 57, English translation.

Probert, William Scott et al., Immunization with Outer Surface Protein (Osp) A, but Not OspC, Provides Cross-Protection of Mice Challenged with North American Isolates of Borrelia burgdorferi, The Journal of Infectious Diseases, 1997, 400-405, 175.

Wallich, Reinhard et al., DNA Vaccines Expressing a Fusion Product of Outer Surface Proteins A and C from Borrelia burgdorferi Induce Protective Antibodies Suitable for Prophylaxis but Not for Resolution of Lyme Disease, Infection and Immunity, 2001, 2130-2136, 69(4).

\* cited by examiner

SEQUENCE LISTING

```
<160> NUMBER OF SEQ ID NOS: 6

<210> SEQ ID NO 1
<211> LENGTH: 822
<212> TYPE: DNA
<213> ORGANISM: Borrelia burgdorferi

<400> SEQUENCE: 1
atgaaaaagt accttttggg aatcggactc attctcgccc tgatcgcctg caagcaaaac      60
gtgtcctccc tcgacgaaaa gaactcagtg tcggtggatc tgcccggcga aatgaaggtg     120
ctcgtgtcca agagaagaa caaggatgga aaatacgacc tgattgccac cgtggacaag     180
ctggagttga agggcacctc agacaagaac aacgggtctg gagtgctgga aggagtcaaa     240
gcggacaagt ccaaggtcaa gctgactatt tcggacgacc tgggccagac taccctggaa     300
gtgttcaagg aggacggaaa gaccctggtg tccaagaagg tcacctccaa ggataagtcg     360
agcaccgaag agaagttcaa tgagaaggga gaagtgtcgg agaagatcat cacccgcgcc     420
gatggaaccc ggctggagta caccgagatc aagtccgatg gttcggggaa ggctaaggaa     480
gtcctgaagg gctacgtgct tgagggtact ctgactgcgg aaaagaccac tctggtggtc     540
aaggaaggca ccgtgactct gtcaaagaac atctccaaga gcggagaagt cagcgtggaa     600
ctgaacgaca cagattcctc cgctgccacg aaaaagaccg ccgcctggaa cagcgggacc     660
agcactctca ccattaccgt gaacagcaaa aagactaagg acctggtgtt caccaaggag     720
aacacgatca ccgtgcagca gtatgactcc aacggtacca agctcgaagg gtccgccgtg     780
gagatcacta agctggacga gattaagaat gcactgaagt ga                       822

<210> SEQ ID NO 2
<211> LENGTH: 273
<212> TYPE: PRT
<213> ORGANISM: Borrelia burgdorferi

<400> SEQUENCE: 2

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110
```

Lys Val Thr Ser Lys Asp Lys Ser Ser Thr Glu Glu Lys Phe Asn Glu
            115                 120                 125

Lys Gly Glu Val Ser Glu Lys Ile Ile Thr Arg Ala Asp Gly Thr Arg
        130                 135                 140

Leu Glu Tyr Thr Glu Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 3
<211> LENGTH: 633
<212> TYPE: DNA
<213> ORGANISM: Borrelia burgdorferi

<400> SEQUENCE: 3

```
atgaagaaga atactctctc cgccattctg atgaccctgt tcctgtttat ctcctgcaac    60
aactccggga aggatggcaa cacctcggcc aactccgccg atgaaagcgt caagggtccc   120
aacctgactg agatctcgaa gaaaatcacc gagtccaacg cggtggtgtt ggcagtgaag   180
gaggtcgaaa ctctgctgac tagcatcgac gagcttgcca aggccattgg aaagaagatt   240
aagaacgacg tgtcactgga caacgaagct gaccataacg gatctcttat ctcgggcgct   300
tacctgattt cgaccctcat caccaagaag atctccgcga tcaaggacag cggggagctc   360
aaggccgaaa ttgagaaagc aaagaagtgc tccgaagagt tcaccgcgaa gctcaaggga   420
gaacacaccg acctgggaaa ggaaggcgtc accgatgata cgcgaagaa ggccatcctc   480
aaaaccaaca acgacaagac aaagggcgcc gacgaactgg agaagctgtt cgagagcgtg   540
aagaatctgt ccaaggccgc caaggaaatg ttgacgaaca gcgtgaagga actgacctcc   600
cctgtggtgg ccgagtcacc gaaaaagcca tga                                633
```

<210> SEQ ID NO 4
<211> LENGTH: 210
<212> TYPE: PRT
<213> ORGANISM: Borrelia burgdorferi

<400> SEQUENCE: 4

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

```
Ile Thr Glu Ser Asn Ala Val Val Leu Ala Val Lys Glu Val Glu Thr
    50                  55                  60

Leu Leu Thr Ser Ile Asp Glu Leu Ala Lys Ala Ile Gly Lys Lys Ile
65                  70                  75                  80

Lys Asn Asp Val Ser Leu Asp Asn Glu Ala Asp His Asn Gly Ser Leu
                85                  90                  95

Ile Ser Gly Ala Tyr Leu Ile Ser Thr Leu Ile Thr Lys Lys Ile Ser
            100                 105                 110

Ala Ile Lys Asp Ser Gly Glu Leu Lys Ala Glu Ile Glu Lys Ala Lys
        115                 120                 125

Lys Cys Ser Glu Glu Phe Thr Ala Lys Leu Lys Gly Glu His Thr Asp
    130                 135                 140

Leu Gly Lys Glu Gly Val Thr Asp Asp Asn Ala Lys Lys Ala Ile Leu
145                 150                 155                 160

Lys Thr Asn Asn Asp Lys Thr Lys Gly Ala Asp Glu Leu Glu Lys Leu
                165                 170                 175

Phe Glu Ser Val Lys Asn Leu Ser Lys Ala Ala Lys Glu Met Leu Thr
            180                 185                 190

Asn Ser Val Lys Glu Leu Thr Ser Pro Val Val Ala Glu Ser Pro Lys
        195                 200                 205

Lys Pro
    210

<210> SEQ ID NO 5
<211> LENGTH: 13
<212> TYPE: DNA
<213> ORGANISM: Borrelia burgdorferi

<400> SEQUENCE: 5
ggcgcgccgc acc                                                              13

<210> SEQ ID NO 6
<211> LENGTH: 143
<212> TYPE: DNA
<213> ORGANISM: Venezuelan equine encephalitis virus (strain TC-83)

<400> SEQUENCE: 6
gtttaaactg taaaacgacg gccagtagtc gtcatagctg tttcctggct acctgagagg         60
ggcccctata actctctacg gctaacctga atggactacg acatagtcta gtccgccaag        120
atatcttcag caccggtggc acc                                                143
```

CANINE LYME DISEASE VACCINE

CROSS-REFERENCE TO RELATED APPLICATIONS

This application is a national stage entry under 35 U.S.C. § 371 of PCT/EP2018/083306, filed on Dec. 3, 2018, which claims priority under 35 U.S.C. § 119(e) of provisional application U.S. Ser. No. 62/594,342 filed Dec. 4, 2017. The contents of PCT/EP2018/083306 are hereby incorporated by reference in their entireties.

FIELD OF THE INVENTION

The present invention relates to new vaccines for canine Lyme disease. Methods of making and using the vaccine alone or in combinations with other protective agents are also provided.

BACKGROUND

Canine Lyme disease is caused by infection with *Borrelia* species (spp.) spirochetes, including primarily *B. burgdorferi* sensu stricto (ss) in the United States and *B. burgdorferi* ss, *B. garinii*, and *B. afzelii* in Europe [Baranton et al., *Int. J. Sys. Bacteriol.* 42:378-383 (1992); Hovius et al., *J. Clin. Microbiol.* 38:2611-2621(2000)]. The spirochetes are transmitted as the infected *Ixodes* spp. ticks obtain a blood meal, and the infection causes clinical signs in canines that range from subclinical synovitis to acute arthritis and arthralgia [Jacobson et al., *Semin. Vet. Med. Surg.* 11:172-182 (1996); Summers et al., *J. Comp. Path.* 133:1-13 (2005)]. Importantly, the incidence of canine Lyme disease cases continues to increase annually coincident with increased numbers of human cases [Haninkova et al., *Emerg. Infect. Dis.* 12:604-610 (2006)]. Moreover, some canine breeds, especially retrievers and bernese mountain dogs, have developed severe glomerulonephritis [Dambach et al., *Vet Pathol* 34:85-96 (1997)], and fatalities from the complication have been reported [Littman et al., *J Vet Intern Med.* 20:422-434 (2006)].

The antibodies produced in response to infection with *Borrelia* spp. have two distinct functions [Schwan, *Biochem. Soc. Trans.* 31:108-112 (2003); Tokarz et al., *Infect. Immun.* 72:5419-5432 (2004)]. The most common humoral immune response is the production of non-specific binding/opsonizing (coating) antibodies that "mark" the spirochete for ingestion by phagocytic cells. Accordingly, this humoral immune response leads to the production of immunoglobulin (Ig)M antibodies that bind and induce a complement-mediated membrane attack complex that kill the foreign antigen. However, the IgM antibody response typically class switches to IgG antibodies that bind the antigen, but no longer stimulate complement-mediated killing. Rather, the IgG antibodies bind to the target antigen and effectively "mark" the spirochete for ingestion by phagocytic cells.

This more typical opsonizing IgG antibody response has not provided effective protection after vaccination, primarily because the proteins that induce the immune response are typically common to multiple other microorganisms, and Lyme disease spirochetes may persist more rarely in the bloodstream [Caine et al., *Infect Immun* 83:3184-3194 (2015)] where interaction with phagocytic cells is likely more effective. Indeed, opsonizing antibodies are induced by several proteins common to other microorganisms (viz. 41 kDa proteins that comprise bacterial flagella), making their value for vaccination-induced antibody-mediated immunity, at best, questionable.

On the other hand, a few *Borrelia* spp. proteins induce an antibody response that maintains the ability to fix complement (borreliacidal) even after switching to IgG antibodies. More specifically, the borreliacidal antibodies bind to the specific protein target and induce complement to form a membrane attack complex that kills the organism, without the necessity of scavenging by phagocytic cells. In contrast to the opsonizing antibodies this borreliacidal response has formed the basis for the most effective canine Lyme disease bacterins.

The earliest canine Lyme disease bacterins provided protection by inducing borreliacidal antibodies specific for *B. burgdorferi* ss outer surface protein (Osp)A [Chu et al., *JAVMA* 201:403-411 (1992); Ma et al., *Vaccine* 14:1366-1374 (1996); Wikle et al., *Intern. J. Appl. Res. Vet. Med.* 4:23-28 (2006); and Straubinger et al., *Vaccine* 20:181-193 (2002)]. The approach can be effective, but it is now understood that the strategy has significant shortcomings that can cause vaccination to fail. For example, the antibodies only recognize *B. burgdorferi* ss spirochetes that are expressing OspA [Jobe et al., *J. Clin. Microbiol.* 32:618-622 (1994); Lovrich et al., *Infect. Immun.* 63:2113-2119 (1995)], and the ticks are also commonly infected with *B. burgdorferi* ss spirochetes that are not expressing OspA [Fikrig et al., *Infect. Immun.* 63:1658-1662 (1995); Ohnishi et al., *Proc. Natl. Acad. Sci.* 98:670-675 (2001)]. In addition, the ticks are commonly also infected with other *Borrelia* spp. such as *B. afzelii* or *B. garinii* [Ornstein et al., *J. Clin. Microbiol.* 39:1294-1298(2001)] that also cause Lyme disease, and the OspA antibodies are genospecies specific [Lovrich et al., *Infect. Immun.* 63:2113-2119 (1995)]. Moreover, the "window of opportunity" for providing protection is short because the expression of OspA, which mediates attachment to the tick midgut [Pal et al., *J Clin Invest* 106:561-569 (2000)], is turned off shortly after the infected tick begins feeding [Schwan et al., *Proc. Natl. Acad. Sci. USA* 92:2909-2913 (1995)].

Coincident with the development of OspA-based canine Lyme disease vaccines, researchers showed that *B. burgdorferi* ss OspC protein also induced protective borreliacidal antibodies [Rousselle et al., *J. Infect. Dis.* 178:733-741 (1998); Ikushima et al., *FEMS Immunol. Med. Microbiol.* 29:15-21 (2000)], but the response was not considered useful for an effective Lyme disease vaccine because OspC, even among *B. burgdorferi* ss isolates collected from the same geographic region, was extremely heterogeneous [Ing-Nang et al., *Genetics* 151:15-30 (1999); Buckles et al., *Clin. Vacc. Immunol.* 13:1162-1165 (2006)]. Therefore, researchers surmised that OspC borreliacidal antibodies would provide antibody-mediated immunity against only a small number of Lyme disease spirochetes.

Consistently, Callister et al., [U.S. Pat. Nos. 6,210,676 and 6,464,985] have suggested employing an immunogenic polypeptide fragment of OspC, specific for the carboxy (C)—terminus of the Osp, alone or in combination with an OspA polypeptide for use in a vaccine to protect humans and other mammals against Lyme disease. Specifically, the strategy was to induce borreliacidal antibodies that bound specifically to a 7 amino acid epitope within the carboxy (C)-terminus of OspC [Jobe et al., *Clin. Diagn. Lab. Immuno.* 10:573-578 (2003); Lovrich et al., *Clin. Diagn. Lab. Immunol.* 12:746-751 (2005)], because the epitope is conserved among each of the *B. burgdorferi* ss strains characterized to date and is also conserved among other pathogenic *Borrelia* spp. (as found in a BLAST search). Therefore, a vaccine that induces OspC borreliacidal antibodies against the conserved epitope would be expected to provide protection against each *B. burgdorferi* ss "strain", regardless of the phyletic characterization of the OspC gene, and also against other canine Lyme disease pathogens such as *B. garinii* or *B. afzelii*. Livey et al. [U.S. Pat. No. 6,872,550] also proposed a vaccine for immunizing against Lyme disease prepared from a combination of recombinant OspA, OspB, and OspC proteins.

Based on this strategy, in 2009, Merck Animal Health, Inc. received USDA approval for a whole cell bacterin, Nobivac® Lyme, comprised of a blend of two separate *B. burgdorferi* isolates that expressed either OspA or OspC on the outer membrane surface, respectively [U.S. Pat. No. 8,137,678 B2; U.S. Pat. No. 8,414,901 B2]. Most significantly, the ability of the Merck Animal Health approach to provide more comprehensive protection against canine Lyme disease with its Nobivac® Lyme vaccine has been well-vetted. For example, researchers confirmed the vaccine induced both OspA and OspC borreliacidal antibodies and also demonstrated that the OspC antibody response includes a significant proportion of borreliacidal antibodies specific for the conserved epitope at the C-terminus [LaFleur et al., *Clin Vaccine Immunol* 16:253-259 (2009)]. Moreover, researchers confirmed the vaccine reliably protected recipient canines for one year post-vaccination [LaFleur et al., *Clin Vacc Immunol* 17:870-874 (2010)] and also showed that the OspC-expressing spirochetes provided significant contribution to the high level of protection [LaFleur et al., *Clin Vacc Immunol* 22:836-839 (2015)]. Despite this improvement, however, there continues to exist a need for more comprehensive and longer term protection, especially as the genetic diversity of Lyme disease-causing spirochetes continues to expand.

More recently, investigators employed an additional strategy to overcome the heterogeneity of OspC and therefore provide more comprehensive protection. This strategy was to perform phylogenetic analyses of OspC from numerous *B. burgdorferi* ss isolates to identify regions within the gene sequences that were homogenous among multiple organisms [Earnhardt et al., *Clin Vaccine Immunol* 14:628-634 (2007)]. The researchers then designed an "artificial" gene that contained the multiple homogenous regions, and used the artificial gene to produce a chimeric protein. The chimeric protein could then be used in a vaccine to presumably induce OspC borreliacidal antibodies that would bind each incorporated region, which would in turn provide more comprehensive protection [Rhodes et al., *Vet J* 198:doi:10.1016/j.tvjl.2013.07.019 (2013)]. The result led to the USDA-approval in 2016 of a commercial canine Lyme disease vaccine (Vanguard® crLyme) comprised of a recombinant (r)OspA and an artificially-produced chimeric protein that contained epitopes from 7 "types" of OspC [Zoetis technical bulletin—SAB-00233]. However, it is not known from the prior art how to prepare a vaccine based on an OspC subunit antigen that could induce borreliacidal antibodies.

A number of vector strategies have been employed through the years, including alphavirus-derived replicon RNA particles (RP) [Frolov et al., PNAS 93: 11371-11377 (1996); Vander Veen, et al. *Anim Health Res Rev.* 13(1):1-9. (2012) doi: 10.1017/S1466252312000011; Kamrud et al., *J Gen Virol.* 91(Pt 7):1723-1727 (2010)] which have been developed from several different alphaviruses, including Venezuelan equine encephalitis virus (VEE) [Pushko et al., *Virology* 239:389-401 (1997)], Sindbis (SIN) [Bredenbeek et al., *Journal of Virology* 67:6439-6446 (1993)], and Semliki Forest virus (SFV) [Liljestrom and Garoff, Biotechnology (NY) 9:1356-1361 (1991)]. RP vaccines deliver propagation-defective alphavirus RNA replicons into host cells and result in the expression of the desired antigenic transgene(s) in vivo [Pushko et al., *Virology* 239(2):389-401 (1997)]. RPs have an attractive safety and efficacy profile when compared to some traditional vaccine formulations [Vander Veen, et al. *Anim Health Res Rev.* 13(1):1-9. (2012)]. The RP platform has been used to encode pathogenic antigens and is the basis for several USDA-licensed vaccines for swine and poultry. In addition, Gipson et al. [*Vaccine*. 21(25-26):3875-84. (2003)] have used the RP platform to encode an OpsA antigen in mouse model vaccination trials, though no comparable trials were reported to have been performed in canines.

Accordingly, despite the increased efficacy provided by the Nobivac® Lyme vaccine and the many presumed dead ends and/or failures of the past, there still remains a long-standing need for a further improved Lyme disease vaccine that will better protect mammals, and especially canines, from this debilitating disease.

The citation of any reference herein should not be construed as an admission that such reference is available as "prior art" to the instant application.

SUMMARY OF THE INVENTION

Accordingly, the present invention provides vectors that encode one or more *Borrelia burgdorferi* antigens. Such vectors can be used in immunogenic compositions comprising these vectors. The immunogenic compositions of the present invention may be used in vaccines. In one aspect of the present invention, a vaccine aids in the protection of the vaccinated subject (e.g., mammal) against Lyme disease. In a particular embodiment of this type, the vaccinated subject is a canine. In another embodiment, the vaccinated subject is a domestic cat. Other domestic mammals may be protected by the vaccines and/or methods of the present invention such as equine (e.g., a horse), and/or bovine. The present invention further provides combination vaccines for eliciting protective immunity against Lyme disease and other diseases, e.g., other canine or equine infectious diseases. Methods of making and using the immunogenic compositions and vaccines of the present invention are also provided.

In specific embodiments, the vector is an alphavirus RNA replicon particle that comprises a nucleic acid construct that encodes a *Borrelia burgdorferi* antigen. In more particular embodiments, the alphavirus RNA replicon particle is a Venezuelan Equine Encephalitis (VEE) alphavirus RNA replicon particle. In still more specific embodiments, the VEE alphavirus RNA replicon particle is a TC-83 VEE alphavirus RNA replicon particle. In other embodiments, the alphavirus RNA replicon particle is a Sindbis (SIN) RNA replicon particle. In still other embodiments, the alphavirus RNA replicon particle is a Semliki Forest virus (SFV) alphavirus RNA replicon particle. In alternative embodiments, a naked DNA expression vector comprises a nucleic acid construct that encodes a *Borrelia burgdorferi* antigen. In yet other alternative embodiments, a naked DNA expression vector comprises an alphavirus replicon sequence that itself encodes a *Borrelia burgdorferi* antigen. The present invention includes all of the nucleic acid constructs of the present invention including synthetic messenger RNA, RNA replicons, as well as all of the alphavirus RNA replicon particles of the present invention, the naked DNA vectors, and the immunogenic compositions and/or vaccines that comprise the nucleic acid constructs (e.g., synthetic messenger RNA, RNA replicons), the alphavirus RNA replicon particles, and/or the naked DNA vectors of the present invention.

In certain embodiments, a nucleic acid construct of the present invention encodes one or more *Borrelia burgdorferi* antigens. In one such embodiment, the *Borrelia burgdorferi* antigen is an outer surface protein A (OspA) or an antigenic fragment thereof. In another embodiment, the *Borrelia burgdorferi* antigen is an outer surface protein C (OspC) or an antigenic fragment thereof. In still other embodiments, the nucleic acid construct encodes two to four *Borrelia burgdorferi* antigens or antigenic fragments thereof.

In certain embodiments of this type, the nucleic acid construct encodes one or more OspAs or one or more antigenic fragments thereof and one or more OspCs or antigenic fragments thereof. In particular, the nucleic acid construct encodes an OspA or an antigenic fragment thereof and an OspC or an antigenic fragment thereof wherein OspA or an antigenic fragment thereof is encoded by a nucleic acid sequence located upstream of a nucleic acid sequence encoding OspC or an antigenic fragment thereof. In another particular embodiment the nucleic acid construct encodes an OspC or an antigenic fragment thereof and an OspA or an antigenic fragment thereof wherein OspC or an antigenic fragment thereof is encoded by a nucleic acid sequence located upstream of a nucleic acid sequence encoding OspA or an antigenic fragment thereof. In other embodiments, the nucleic acid construct encodes OspA or an antigenic fragment thereof, originating from two or more *Borrelia burgdorferi* strains. In still other embodiments, the nucleic acid construct encodes an OspC or an antigenic fragment thereof originating from two or more *Borrelia burgdorferi* strains. The present invention further provides alphavirus RNA replicon particles that comprise any of these nucleic acid constructs. In alternative embodiments, the vector is a naked DNA that comprises one or more of these nucleic acid constructs.

In particular embodiments, immunogenic compositions comprise alphavirus RNA replicon particles that comprise a nucleic acid construct that encodes one or more *Borrelia burgdorferi* antigens or antigenic fragments thereof. In related embodiments, the immunogenic compositions comprise alphavirus RNA replicon particles that comprise a nucleic acid construct that encodes two to four *Borrelia burgdorferi* antigens or antigenic fragments thereof.

In specific embodiments, the immunogenic compositions comprise alphavirus RNA replicon particles that comprise a nucleic acid construct of the present invention. In particular embodiments of this type, the alphavirus RNA replicon particles comprise a nucleic acid construct encoding an OspA. In related embodiments, the alphavirus RNA replicon particles comprise a nucleic acid construct encoding an antigenic fragment of an OspA. In still other embodiments, the alphavirus RNA replicon particles comprise a nucleic acid construct encoding OspAs or antigenic fragments thereof from two or more different *Borrelia burgdorferi* strains. In other embodiments, the alphavirus RNA replicon particles comprise a nucleic acid construct encoding an OspC. In related embodiments, the alphavirus RNA replicon particles comprise a nucleic acid construct encoding an antigenic fragment of an OspC. In still other embodiments, the alphavirus RNA replicon particles comprise a nucleic acid construct encoding OspCs or antigenic fragments thereof from two or more different *Borrelia burgdorferi* strains.

In yet other embodiments, the immunogenic compositions comprise alphavirus RNA replicon particles that comprise a nucleic acid construct encoding a combination of two or more of the following *Borrelia burgdorferi* antigens: OspA from one or more strains, OspC from one or more strains, and/or antigenic fragments of any of these proteins. In particular embodiments, the immunogenic composition comprises alphavirus RNA replicon particles that are all Venezuelan Equine Encephalitis (VEE) alphavirus RNA replicon particles.

In related embodiments, the immunogenic composition comprises two or more sets of alphavirus RNA replicon particles. In particular embodiments of this type, one set of alphavirus RNA replicon particles comprises a first nucleic acid construct, whereas the other set of alphavirus RNA replicon particles comprise a second nucleic acid construct. In yet other embodiments, the immunogenic composition comprises one set of alphavirus RNA replicon particles that comprise a first nucleic acid construct, another set of alphavirus RNA replicon particles that comprise a second nucleic acid construct, and a third set of alphavirus RNA replicon particles that comprise a third nucleic acid construct. In still other embodiments, the immunogenic composition comprises one set of alphavirus RNA replicon particles that comprise a first nucleic acid construct, another set of alphavirus RNA replicon particles that comprise a second nucleic acid construct, a third set of alphavirus RNA replicon particles that comprise a third nucleic acid construct, and a fourth set of alphavirus RNA replicon particles that comprise a fourth nucleic acid construct. In yet other embodiments, the immunogenic composition comprises a set of alphavirus RNA replicon particles that comprise a first nucleic acid construct, another set of alphavirus RNA replicon particles that comprise a second nucleic acid construct, a third set of alphavirus RNA replicon particles that comprise a third nucleic acid construct, a fourth set of alphavirus RNA replicon particles that comprise a fourth nucleic acid construct, and a fifth set of alphavirus RNA replicon particles that comprise a fifth nucleic acid construct. In such embodiments, the nucleotide sequences of the first nucleic acid construct, the second nucleic acid construct, third nucleic acid construct, the fourth nucleic acid construct, and the fifth nucleic acid construct are all different.

Accordingly, the present invention provides immunogenic compositions comprising two or more alphavirus RNA replicon particles each individually encoding one or more *Borrelia burgdorferi* antigens. In particular embodiments of this type, one alphavirus RNA replicon particle encodes a *Borrelia burgdorferi* outer surface protein A (OspA) or an antigenic fragment thereof. In certain embodiments, one alphavirus RNA replicon particle encodes a *Borrelia burgdorferi* outer surface protein C (OspC) or an antigenic fragment thereof. In yet another embodiment, one alphavirus RNA replicon particle encodes a *Borrelia burgdorferi* OspA or an antigenic fragment thereof, and a second alphavirus RNA replicon particle encodes a *Borrelia burgdorferi* OspC or an antigenic fragment thereof. In related embodiments, an immunogenic composition further comprises alphavirus RNA replicon particles that comprise a nucleic acid construct that encode two or more *Borrelia burgdorferi* antigens or antigenic fragments thereof.

In particular, the present invention provides immunogenic compositions comprising a first and a second alphavirus RNA replicon particle each individually encoding an OspA or an antigenic fragment thereof and an OspC or an antigenic fragment thereof (dual constructs) wherein the first RNA replicon particle comprises a nucleic acid sequence encoding OspA or an antigenic fragment thereof that is located upstream of a nucleic acid sequence encoding OspC or an antigenic fragment thereof, and the second RNA replicon particle comprises a nucleic acid sequence encoding OspC or an antigenic fragment thereof that is located upstream of a nucleic acid sequence encoding OspA or an antigenic fragment thereof.

In particular embodiments, the nucleic acid construct encodes an OspA, or antigenic fragment thereof, originating from *B. burgdorferi* strain 297. In specific embodiments of this type, the OspA comprises an amino acid sequence comprising 95% identity or more with the amino acid sequence of SEQ ID NO: 2. In more specific embodiments, the OspA comprises the amino acid sequence of SEQ ID NO: 2. In even more specific embodiments, the OspA is encoded by the nucleotide sequence of SEQ ID NO: 1.

In a related embodiment, the nucleic acid construct encodes an OspC, or antigenic fragment thereof, originating from *B. burgdorferi* strain 50772 (ATCC No. PTA-439). In specific embodiments of this type, the OspC comprises an amino acid sequence comprising 95% identity or more with the amino acid sequence of SEQ ID NO: 4. In more specific embodiments, the OspC comprises the amino acid sequence of SEQ ID NO: 4. In even more specific embodiments, the OspC is encoded by the nucleotide sequence of SEQ ID NO: 3. In yet other embodiments, the nucleic acid construct encodes an OspA originating from *B. burgdorferi* strain 297 and an OspC originating from *B. burgdorferi* strain 50772.

The present invention comprises vaccines comprising the immunogenic compositions of the present invention, more specifically the vaccines are nonadjuvanted vaccines. In particular embodiments, the vaccine aids in the prevention of disease due to *B. burgdorferi*. In specific embodiments, the disease due to *B. burgdorferi* is Lyme disease. In more specific embodiments, the Lyme disease is canine Lyme disease. In particular embodiments a vaccine of the present invention is effective for the vaccination of healthy canine 6-8 weeks of age against canine Lyme disease. In specific embodiments of this type, a vaccine of the present invention is effective for the vaccination of healthy canine, 7 weeks of age against canine Lyme disease. In certain embodiments, antibodies are induced in a canine when the canine is immunized with the vaccine. In particular embodiments, the antibodies are opsonizing IgG. In other embodiments, the antibodies induced are borreliacidal. In still other embodiments, both opsonizing IgG and borreliacidal antibodies are induced. In more specific embodiments, the OspA antibodies induced are borreliacidal and opsonizing IgG and the OspC antibodies induced are borreliacidal and opsonizing IgG.

In certain embodiments, a vaccine of the present invention further comprises at least one non-*Borrelia* immunogen for eliciting protective immunity to a non-*Borrelia* pathogen. In particular embodiments, a vaccine of the present invention further comprises an alphavirus RNA replicon particle that encodes at least one protein antigen from the non-*Borrelia* immunogen for eliciting protective immunity to a non-*Borrelia* pathogen. In certain embodiments, the non-*Borrelia* immunogen is from a non-*Borrelia* pathogen such as a canine distemper virus, a canine adenovirus, a canine parvovirus, a canine parainfluenza virus, a canine coronavirus, a canine influenza virus, a *Leptospira* serovar, an *Leishmania* organism, a *Bordetella bronchiseptica*, a *Mycoplasma* species, a rabies virus, an *Ehrlichia canis*, an *Anaplasma* organism, and/or a combination thereof.

In particular embodiments, the non-*Borrelia* immunogen from a *Leptospira* serovar is a *Leptospira kirschneri* serovar grippotyphosa. In other embodiments, the immunogen from a *Leptospira* serovar is a *Leptospira interrogans* serovar canicola. In still other embodiments, the immunogen from a *Leptospira* serovar is a *Leptospira interrogans* serovar icterohaemorrhagiae. In yet other embodiments, the immunogen from a *Leptospira* serovar is a *Leptospira interrogans* serovar pomona. In still other embodiments, the vaccine comprises immunogens from multiple *Leptospira* serovars. In particular embodiments, the non-*Borrelia* immunogen from a *Mycoplasma* species is *Mycoplasma cynos*.

The present invention further provides methods of immunizing a mammal against a pathogenic *Borrelia* genospecies comprising administering to the mammal an immunologically effective amount of the vaccine of the present invention. In particular embodiments, the vaccine is administered by subcutaneous injection. In alternative embodiments, the vaccine is administered by intramuscular injection. In other embodiments, the vaccine is administered by intravenous injection. In still other embodiments, the vaccine is administered by intradermal injection. In yet other embodiments, the vaccine is administered by oral administration. In still other embodiments, the vaccine is administered by intranasal administration. In specific embodiments, the mammal is a canine. In other embodiments, the mammal is an equine (e.g., a horse)

The vaccines of the present invention can be administered as a primer vaccine and/or as a booster vaccine. In certain embodiments, in the case of the administration of both a primer vaccine and a booster vaccine, the primer vaccine and the booster vaccine can be administered by the identical route. In certain embodiments of this type, the primer vaccine and the booster vaccine are both administered by subcutaneous injection. In alternative embodiments, in the case of the administration of both a primer vaccine and a booster vaccine, the administration of the primer vaccine can be performed by one route and the booster vaccine by another route. In certain embodiments of this type, the primer vaccine can be administered by subcutaneous injection and the booster vaccine can be administered orally.

A vaccine composition of the present invention can further include an immunologically effective amount of inactivated organisms from one or more additional strains (which may be collectively labeled herein as the second strain), from a pathogenic *Borrelia* genospecies. In particular embodiments, the second strain exhibits OspA and OspB antigens. Examples of appropriate second strains include one or more of the following: *B. burgdorferi* ss S-1-10 (ATCC No. PTA-1680), *B. burgdorferi* ss B-31 (ATCC No. 35210), *B. afzelii* (e.g., available as ATCC No. 51567) *B. garinii* (e.g., available as ATCC Nos. 51383 and 51991), *B. burgdorferi* ss DK7, *B. burgdorferi* ss 61BV3, *B. burgdorferi* ss ZS7, *B. burgdorferi* ss Pka, *B. burgdorferi* ss IP1, IP2,IP3, *B. burgdorferi* ss HII, *B. burgdorferi* ss P1F, *B. burgdorferi* ss Mil, *B. burgdorferi* ss 20006, *B. burgdorferi* ss 212, *B. burgdorferi* ss ESP1, *B. burgdorferi* ss Ne-56, *B. burgdorferi* ss Z136, *B. burgdorferi* ss ia, and/or any combinations thereof.

The present invention further provides a method of immunizing a mammal, against pathogenic *Borrelia* spp., specifically *B. burgdorferi* ss, comprising injecting the mammal with an immunologically effective amount of the above described inventive vaccines. In particular embodiments the vaccines can include from about $1 \times 10^4$ to about $1 \times 10^{10}$ RPs or higher, for example. In more particular embodiments the vaccines can include from about $1 \times 10^5$ to about $1 \times 10^9$ RPs. In even more particular embodiments the vaccines can include from about $1 \times 10^6$ to about $1 \times 10^8$ RPs. In particular embodiments, after vaccination, the immunized mammal produces borreliacidal antibodies. In particular embodiments the mammal is a canine. In other embodiments the mammal is an equine (e.g., a horse).

In certain embodiments the vaccines of the present invention are administered in 0.05 mL to 3 mL doses. In more particular embodiments the dose administered is 0.1 mL to 2 mLs. In still more particular embodiments the dose administered is 0.2 mL to 1.5 mLs. In even more particular embodiments the dose administered is 0.3 to 1.0 mLs. In still more particular embodiments the dose administered is 0.4 mL to 0.8 mLs.

The present invention further provides combination vaccines that further include vectors (e.g., alphavirus RNA replicon particles) encoding one or more immunogens from other canine pathogens, including, e.g., immunogens for eliciting immunity to canine distemper virus, canine adenovirus, canine parvovirus, canine parainfluenza virus, canine coronavirus, canine influenza virus, and/or *Leptospira* serovars, e.g., *Leptospira kirschneri* serovar grippotyphosa, *Leptospira interrogans* serovar *canicola*, *Leptospira interrogans* serovar *icterohaemorrhagiae*, and/or *Leptospira interrogans* serovar *pomona*. Additional canine pathogens that can be added to a combination vaccine of the present invention include *Leishmania* organisms such as *Leishmania major* and *Leishmania infantum*, *Bordetella bronchiseptica*, a *Mycoplasma* species (e.g., *Mycoplasma cynos*), rabies virus, *anaplasma* species such as *Anaplasma phagocytophilum* and *Anaplasma* platys; and *Ehrlichia canis*. In particular embodiments, a vaccine of the present invention further comprises an alphavirus RNA replicon particle that encodes at least one or more antigens from one or more such immunogens.

These and other aspects of the present invention will be better appreciated by reference to the following Detailed Description.

DETAILED DESCRIPTION OF THE INVENTION

The present invention provides immunogenic compositions and/or vaccines that include an immunologically effective amount of an alphavirus RNA replicon particle encoding a *Borrelia burgdorferi* outer surface protein A (OspA) or an antigenic fragment thereof and a *Borrelia burgdorferi* outer surface protein C (OspC) or an antigenic fragment thereof, an immunologically effective amount of two or more vectors, with at least one alphavirus RNA replicon particle encoding a *Borrelia burgdorferi* outer surface protein A (OspA) or an antigenic fragment thereof and at least another alphavirus RNA replicon particle encoding a *Borrelia burgdorferi* outer surface protein C (OspC) or an antigenic fragment thereof, or a combination of the alphavirus RNA replicon particles that encode both Osp A or an antigenic fragment thereof and OspB or an antigenic fragment thereof, with alphavirus RNA replicon particles that encode Osp A or an antigenic fragment thereof and/or encode Osp C or an antigenic fragment thereof. All of such immunogenic compositions may be used in mammalian vaccines. In one aspect of the present invention, the vaccine aids in the protection of the vaccinated subject (e.g., mammal) against Lyme disease. In a particular embodiment of this type, the vaccinated subject is a canine. Accordingly, the present invention provides new immunologic compositions that improve the reliability of vaccination to prevent canine Lyme disease by (i) significantly reducing the potential for untoward side effects by eliminating vaccination with unrelated antigens from bacterins and (ii) still provide comprehensive protection. The Lyme Disease vaccine formulations of the present invention should also significantly lengthen the "window of effectiveness" by inducing an effective anamnestic memory response.

In order to more fully appreciate the invention, the following definitions are provided.

The use of singular terms for convenience in description is in no way intended to be so limiting. Thus, for example, reference to a composition comprising "a polypeptide" includes reference to one or more of such polypeptides. In addition, reference to an "organism" includes reference to a plurality of such organisms, unless otherwise indicated.

As used herein the term "approximately" is used interchangeably with the term "about" and signifies that a value is within fifty percent of the indicated value i.e., a composition containing "approximately" $1 \times 10^8$ alphavirus RNA replicon particles per milliliter contains from $5 \times 10^7$ to $1.5 \times 10^8$ alphavirus RNA replicon particles per milliliter.

As used herein the term, "canine" includes all domestic dogs, *Canis lupus familiaris* or *Canis familiaris*, unless otherwise indicated.

The term "genospecies," was first used and defined by G. Baranton et al., 1992, *International J. of Systematic Bacteriology* 42: 378-383, and is used herein in the same way that the term, "species" is employed in describing the taxonomy of non-*Borrelia* organisms.

The term "non-*Borrelia*", is used to modify terms such as organism, pathogen, and/or antigen (or immunogen) to signify that the respective organism, pathogen, and/or antigen (or immunogen) is not a *Borrelia* organism, not a *Borrelia* pathogen, and/or not a *Borrelia* antigen (or immunogen) respectively, and that a non-*Borrelia* protein antigen (or immunogen) does not originate from a *Borrelia* organism.

The terms "originate from", "originates from" and "originating from" are used interchangeably with respect to a given protein antigen and the pathogen or strain of that pathogen that naturally encodes it, and as used herein signify that the unmodified and/or truncated amino acid sequence of that given protein antigen is encoded by that pathogen or strain of that pathogen. The coding sequence, within a nucleic acid construct of the present invention for a protein antigen originating from a pathogen may have been genetically manipulated so as to result in a modification and/or truncation of the amino acid sequence of the expressed protein antigen relative to the corresponding sequence of that protein antigen in the pathogen or strain of pathogen (including naturally attenuated strains) it originates from.

"Standard growth conditions" for culturing *Borrelia* genospecies require growth at a temperature ranging from about 33° C. to about 35° C., in BSK (Barbour Stoenner Kelly) medium. BSK medium as described herein was prepared according to Callister et al. [*Detection of Borreliacidal Antibodies by Flow Cytometry*, Sections 11.5.1-11.5.12, *Current Protocols in Cytometry*, John Wiley and Sons, Inc. Supplement 26, (2003) hereby incorporated by reference herein in its entirety]. (BSK medium is also commercially available, e.g., from Sigma, St. Louis, MO).

As used herein "OspC7" is an immunodominant OspC borreliacidal antibody epitope located in a 7 amino acid region [Lovrich et al., *Clin. Diagn. Lab. Immunol.*, 12:746-751, (2005)] within the C-terminal 50 amino acids of OspC, as disclosed by Callister et al. [U.S. Pat. No. 6,210,676 B1 and U.S. Pat. No. 6,464,985 B1 that is conserved among the known pathogenic *Borrelia* spp. This conservation is readily confirmed by a BLAST search of the codon segment encoding the 7 amino acid segment described by Lovrich et al.

[*Clin. Diagn. Lab. Immunol.,* 12:746-751, (2005)]. Such a search, when conducted on Oct. 9, 2006 generated a results list of 100 *Borrelia* species containing the above noted OspC 7-mer epitope coding segment. In particular embodiments, an alphavirus RNA replicon particle encodes an antigenic fragment of Osp C that comprises OspC7.

As used herein, the terms "protecting" or "providing protection to" or "eliciting protective immunity to" and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, a "vaccine" is a composition that is suitable for application to an animal, e.g., a canine, feline, or equine (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, a multivalent vaccine is a vaccine that comprises two or more different antigens. In a particular embodiment of this type, the multivalent vaccine stimulates the immune system of the recipient against two or more different pathogens.

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "alphavirus RNA replicon particle", abbreviated "RP", is an alphavirus-derived RNA replicon packaged in structural proteins, e.g., the capsid and glycoproteins, which also are derived from an alphavirus, e.g., as described by Pushko et al., [*Virology* 239(2):389-401 (1997)]. An RP cannot propagate in cell cultures or animal hosts (without a helper plasmid or analogous component), because the replicon does not encode the alphavirus structural components (e.g., capsid and glycoproteins). The heterologous nucleic acid sequences in the RNA RPs encoding OspA and/or OspC, or antigenic fragments thereof, are under the transcriptional control of an alphavirus subgenomic (sg) promoter, in particular the 26S sg promoter, preferably the VEEV 26S sg promoter.

In case of dual RP constructs of OspA and OspC coding sequences, each of the coding sequences in a construct can be under the transcriptional control of separate subgenomic promoters. In such a dual construct the upstream coding sequence corresponds to the 5' promoter position and the downstream coding sequence corresponds to the 3' promoter position (positive sense RNA; FIGS. 1 and 2). Preferably the upstream- and downstream coding sequences are adjacent.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., canine.

Parenteral administration" includes subcutaneous injections, submucosal injections, intravenous injections, intramuscular injections, intradermal injections, and infusion.

As used herein the term "antigenic fragment" in regard to a particular protein (e.g., a protein antigen) is a fragment of that protein (including large fragments that are missing as little as a single amino acid from the full-length protein) that is antigenic, i.e., capable of specifically interacting with an antigen recognition molecule of the immune system, such as an immunoglobulin (antibody) or T cell antigen receptor. For example, an antigenic fragment of an outer surface protein A (OspA) is a fragment of the OspA protein that is antigenic. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity of the full length protein. In preferred embodiments, an antigenic fragment retains at least 50% of the antigenicity of the full length protein. In more preferred embodiments, it retains at least 75% of the antigenicity of the full length protein. Antigenic fragments can be as small as 7-20 amino acids (see above) or at the other extreme, be large fragments that are missing as little as a single amino acid from the full-length protein. In particular embodiments, the antigenic fragment comprises 25 to 150 amino acid residues. In other embodiments, the antigenic fragment comprises 50 to 250 amino acid residues.

An "OspC-specific borreliacidal antibody" is one that is found, e.g., in the serum of an animal vaccinated with *B. burgdorferi* ss 50772 (ATCC No. PTA-439), and is one that selectively binds to any epitope of the OspC antigen and kills the spirochetes dependent or independent of complement. An "OspC7-specific borreliacidal antibody" is one that is found, e.g., in the serum of an animal vaccinated with *B. burgdorferi* ss 50772 (ATCC No. PTA-439), and is one that selectively binds to the 7 C-terminal amino acids of OspC as described by Lovrich et al. [*Clin. Diagn. Lab. Immunol.,* 12:746-751, (2005)] and kills the spirochetes (generally by inducing a complement-mediated membrane attack complex). The specificity of OspC borreliacidal antibodies has been well-established. For example, OspC borreliacidal antibodies are detected commonly in Lyme disease sera by measuring the susceptibility of *B. burgdorferi* ss 50772 in a borreliacidal antibody test. Sera from human patients with closely-related illnesses only rarely (2%) contain cross-reactive antibodies that also kill strain 50772 [described in detail by Callister, et al., *Clinical and Diagnostic Laboratory Immunology* 3(4): 399-4021(1996)]. Moreover, a peptide ELISA that uses the OspC7 borreliacidal epitope accurately captures borreliacidal antibodies in Lyme disease sera, and sera from patients with other closely related illnesses only rarely (<2%) contain cross-reactive antibodies that also bind the OspC7 peptide.

When a "significant proportion" of the OspC-specific borreliacidal antibodies in sera induced by a vaccine are specific for the conserved epitope OspC7, it means that there is a measurable reduction in the OspC-specific borreliacidal antibodies in the sera following the absorption of that sera with OspC7. It is preferably defined as at least a 2-fold reduction in the borreliacidal antibody titer of the sera detected by using *B. burgdorferi* ss 50772, and more preferably as a 2- to 4-fold, or greater reduction in the borreliacidal antibody titer of the sera following the absorption of that sera with OspC7.

A "complement specific reaction" is an antibody reaction that requires serum complement to be present in order for *Borrelia* spp. organism(s) to be killed by a borreliacidal antibody.

As used herein, the term "inactivated" microorganism is used interchangeably with the term "killed" microorganism. For the purposes of this invention, an "inactivated" *Borrelia burgdorferi* ss organism is an organism which is capable of eliciting an immune response in an animal, but is not capable of infecting the animal. The *Borrelia burgdorferi* ss isolates may be inactivated by an agent selected from the group consisting of binary ethyleneimine, formalin, beta-propiolactone, thimerosal, or heat. In a particular embodiment, the *Borrelia burgdorferi* ss isolates are inactivated by binary ethyleneimine.

As used herein, a "nonadjuvanted vaccine" is a vaccine or a multivalent vaccine that does not contain an adjuvant.

*B. burgdorferi* ss 50772 (ATCC No. PTA-439) as stated in U.S. Pat. No. 6,210,676, and *B. burgdorferi* ss S-1-10 (ATCC No. PTA-1680) as stated in U.S. Pat. No. 6,316,005, were deposited with the American Type Culture Collection, 10801 University Boulevard Manassas (Va.) 20110 on Jul. 30, 1999, and Apr. 11, 2000, respectively.

As used herein one amino acid sequence is 100% "identical" or has 100% "identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, NC 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wisconsin) pileup program using the default parameters.

It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

Alternative OspA Strains

Strains providing the OspA antigen, can be a conventional pathogenic laboratory *B. burgdorferi* ss isolate [Barbour et al., *J. Clin. Microbiol.* 52:478-484 (1985)] such as *B. burgdorferi* ss B-31 (ATCC No. 35210). A particular second organism is the exemplified *B. burgdorferi* ss S-1-10 strain (ATCC No. PTA-1680). Additional strains suitable for use as the second organism for vaccine compositions optimized for regions outside of North America include, e.g., the strains: *B. burgdorferi* ss B-31 (ATCC No. 35210), *B. afzelii* (e.g., available as ATCC No. 51567) and *B. garinii* (e.g., available as ATCC Nos. 51383 and 51991), as well as those listed in Table 1 below.

TABLE 1

| Strain | Country | Cultured from |
|---|---|---|
| *B. burgdorferi* ss DK7 [1] | Denmark | skin |
| *B. burgdorferi* ss 61BV3 [1] | Germany | skin |
| *B. burgdorferi* ss ZS7 [1] | Switzerland | tick |
| *B. burgdorferi* ss Pka [1] | Germany | tick |
| *B. burgdorferi* ss IP1, IP2, IP3 [1] | France | CSF |
| *B. burgdorferi* ss HII [1] | Italy | blood |
| *B. burgdorferi* ss P1F [1] | Switzerland | synovia |
| *B. burgdorferi* ss Mil [1] | Slovakia | tick |
| *B. burgdorferi* ss 20006 [1] | France | tick |
| *B. burgdorferi* ss 212 [1] | France | tick |
| *B. burgdorferi* ss ESP1 [1] | Spain | tick |
| *B. burgdorferi* ss Ne-56 [1] | Switzerland | tick |
| *B. burgdorferi* ss Z136 [1] | Germany | tick |
| *B. burgdorferi* ss ia [2] | Finland | CSF |

[1] Lagal et al., *J. Clin. Microbiol.* 41: 5059-5065 (2003)
[2] Heikkila et al., *J. Clin. Microbiol.* 40: 1174-1180 (2002)

The vaccine composition is readily administered by any standard route including intravenous, intramuscular, subcutaneous, oral, intranasal, intradermal, and/or intraperitoneal vaccination. The artisan will appreciate that the vaccine composition is preferably formulated appropriately for each type of recipient animal and route of administration.

Thus, the present invention also provides methods of immunizing a canine against *B. burgdorferi* ss and other *Borrelia* spp. One such method comprises injecting a canine with an immunologically effective amount of a vaccine of the present invention, so that the canine produces appropriate OspA and/or OspC. In particular embodiments the antibodies are borreliacidal antibodies.

EXAMPLES

The following examples serve to provide further appreciation of the invention, but are not meant in any way to restrict the effective scope of the invention.

Example 1

Construction of OspA and OspC Vaccines Delivered by Alphavirus RNA Replicon Particles RNA viruses have been used as vector-vehicles for introducing vaccine antigens, which have been genetically engineered into their genomes. However, their use to date has been limited primarily to incorporating viral antigens into the RNA virus and then introducing the virus into a recipient host. The result is the induction of protective antibodies against the incorporated viral antigens. For example, the alphavirus replicon vector has been used to protect mice against botulinum neurotoxin and anthrax via expression of *C. botulinum* neurotoxin Hc or the *B. anthracis* protective antigen, respectively [Lee et al., *Vaccine* 24(47-48) 6886-6892 (2006)]. Alphavirus RNA replicon particles have been used to encode pathogenic antigens. Such alphavirus replicon platforms have been developed from several different alphaviruses, including Venezuelan equine encephalitis virus (VEE) [Pushko et al., Virology 239:389-401 (1997)], Sindbis (SIN) [Bredenbeek et al., *Journal of Virology* 67:6439-6446 (1993) the contents of which are hereby incorporated herein in their entireties], and Semliki Forest virus (SFV) [Liljestrom and Garoff, *Biotechnology* (NY) 9:1356-1361 (1991), the contents of which are hereby incorporated herein in their entireties]. Moreover, alphavirus RNA replicon particles are the basis for several USDA-licensed vaccines for swine and poultry. These include: Porcine Epidemic Diarrhea Vaccine, RNA Particle (Product Code 19U5.P1), Swine Influenza Vaccine, RNA (Product Code 19A5.D0), Avian Influenza Vaccine, RNA (Product Code 1905.D0), and Prescription Product, RNA Particle (Product Code 9PP0.00). As disclosed below, the ability of an alphavirus RNA replicon vector system to induce canines to produce borreliacidal antibodies specific for OspA, OspC, and DbpA has been examined.

Incorporation of the Coding Sequences for OspA or OspC, into the Alphavirus Replicon:

Amino acid sequences for OspA (strain 297), and OspC (strain 50772) were used to generate codon-optimized (*Canis lupus* codon usage) nucleotide sequences in silico. Optimized sequences were prepared as synthetic DNA by a commercial vendor (ATUM, Newark, CA).

The VEE replicon vectors designed to express OspA or OspC were constructed as previously described [see, U.S. Pat. No. 9,441,247 B2; the contents of which are hereby incorporated herein by reference], with the following modifications. The TC-83-derived replicon vector "pVEK" [disclosed and described in U.S. Pat. No. 9,441,247 B2] was digested with restriction enzymes Ascl and Pacl. A DNA plasmid containing the codon-optimized open reading frame sequence of the OspA, or OspC, with 5' flanking sequence (5'-GGCGCGCCGCACC-3') [SEQ ID NO: 5] and 3' flanking sequence (5'-TTAAT-TAA-3'), was similarly digested with restriction enzymes Ascl and Pacl. The synthetic gene cassette was then ligated into the digested pVEK vector, and the resulting clones were renamed "pVHV-OspA" and "pVHV-OspC".

Production of TC-83 RNA replicon particles (RP) was conducted according to methods previously described [U.S. Pat. No. 9,441,247 B2 and U.S. Pat. No. 8,460,913 B2; the contents of which are hereby incorporated herein by reference]. Briefly, pVHV replicon vector DNA and helper DNA plasmids were linearized with Notl restriction enzyme prior to in vitro transcription using MegaScript T7 RNA polymerase and cap analog (Promega, Madison, WI). Importantly, the helper RNAs used in the production lack the VEE subgenomic promoter sequence, as previously described [Kamrud et al., *J Gen Virol.* 91(Pt 7):1723-1727 (2010)]. Purified RNA for the replicon and helper components were combined and mixed with a suspension of Vero cells, electroporated in 4 mm cuvettes, and returned to serum-free cell culture media obtained from Thermo Fisher, Waltham MA sold under the name OptiPro SFM®. Following overnight incubation, alphavirus RNA replicon particles were purified from the cells and media by passing the suspension through a ZetaPlus BioCap depth filter (3M, Maplewood, MN), washing with phosphate buffered saline containing 5% sucrose (w/v), and finally eluting the retained RP with 400 mM NaCl buffer. Eluted RP were formulated to a final 5% sucrose (w/v), passed through a 0.22 micron membrane filter, and dispensed into aliquots for storage. Titer of functional RP was determined by immunofluorescence assay on infected Vero cell monolayers. Batches of RP were identified according to the gene encoded by the packaged replicon: RP-OspA or RP-OspC.

Example 2

Vaccine with RP-OspA Construct

Materials and Methods

Construct:

The RP-OspA construct was produced as described above using a nucleotide sequence encoding an antigen comprising the immunogenic epitopes of outer surface protein A.

Animals:

Five month old beagles (Marshall Bioresources) were housed communally in raised dog runs, and food and water was available ad libitum.

Preparation of the RP-OspA Vaccine:

The OspA RNA was electroporated in conjunction with helper RNAs into Vero cells. The OspA was packaged into RPs following the co-electroporation process generating the RP-OspA. The RP-OspA was then blended with stabilizer (sucrose, N-Z Amine, gelatin), 0.9% saline, amphotericin B, and gentamicin so that a 1.0 mL dose contained a target of $1.0 \times 10^8$ replicon particles/mL. The vaccine was then freeze dried.

Vaccination and Collection of Serum:

Dogs were vaccinated subcutaneously in the neck with a 1 mL dose of the RP-OspA vaccine and boosted with an additional 1 mL dose after 21 days. Whole blood was collected on study days 7, 14, 20, 29, 35, and 42 by venipuncture of the jugular vein. The serum was separated by centrifugation and stored at −10° C. or colder until tested.

Detection of OspA Borreliacidal Antibodies:

OspA borreliacidal antibodies were detected using a flow cytometric procedure and *B. burgdorferi* ss S-1-10 [Callister et al., Arch. Intern. Med. 154:1625-1632 (1994)].

Detection of OspA IgG Antibodies:

OspA IgG opsonizing antibodies were detected by ELISA.

Results

Vaccination with the RP-OspA vaccine reliably induced high levels of IgG antibodies, and the antibody response included a significant amount of borreliacidal OspA antibodies at 2 weeks post-booster vaccination.

TABLE 2

Mean Antibody Titers (n = 5) after Vaccination with RP-OspA

| Antibody Type | Day −1 | Day 35 |
|---|---|---|
| IgG | ND[a] | 7610 |
| Borreliacidal | ND[a] | 3044 |

[a]ND = none detected

The results in Table 2 above, demonstrate the ability of a vaccine comprising RP-OspA to induce significant levels of OspA borreliacidal antibodies.

Example 3

Vaccine with RP-OspC Construct

Materials and Methods

Construct:

The RP-OspC construct was produced as described above using a nucleotide sequence encoding an antigen comprising the immunogenic epitopes of outer surface protein C.

Animals:

Five month old beagles (Marshall Bioresources) were housed communally in raised dog runs, and food and water was available ad libitum.

Preparation of the RP-OspC Vaccine:

The OspC RNA was electroporated in conjunction with helper RNAs into Vero cells. The OspC was packaged into RPs following the co-electroporation process generating the RP-OspC. The RP-OspC was then blended with stabilizer (sucrose, N-Z Amine, gelatin), 0.9% saline, amphotericin B, and gentamicin so that a 1.0 mL dose contained a target of $1.0\times10^8$ replicon particles/mL. The vaccine was then freeze dried.

Vaccination and Collection of Serum:

Dogs were vaccinated subcutaneously in the neck with a 1 mL dose of the RP-OspC vaccine and boosted with an additional 1 mL dose after 21 days. Whole blood was collected on study days 7, 14, 20, 29, 35, and 42 by venipuncture of the jugular vein. The serum was separated by centrifugation and stored at −10° C. or colder until tested.

Detection of OspC Borreliacidal Antibodies:

OspC borreliacidal antibodies were detected using a flow cytometric procedure and *B. burgdorferi* ss 50772 [Callister et al., Arch. Intern. Med. 154:1625-1632 (1994)].

Detection of OspC IgG Antibodies:

OspC IgG antibodies were detected by ELISA.

Results

Vaccination with the RP-OspC vaccine reliably induced high levels of IgG antibodies, and the antibody response included a significant amount of borreliacidal OspC antibodies at 2 weeks post-booster vaccination.

TABLE 3

Mean Antibody Titers (n = 5) after Vaccination with RP-OspC

| Antibody Type | Day −1 | Day 35 |
|---|---|---|
| IgG | ND[a] | 696 |
| Borreliacidal | ND[a] | 1940 |

[a]ND = none detected

The results demonstrate the ability of a vaccine comprising RP-OspC to induce significant levels of OspC borreliacidal antibodies.

Example 4

Combination Vaccine with RP-OspA and RP-OspC

Materials and Methods

Construct:

The RP-OspA and RP-OspC constructs were produced as described above.

Animals:

Five month old beagles (Marshall Bioresources) were housed communally in raised dog runs, and food and water was available ad libitum.

Preparation of the RP-OspA, and RP-OspC Combination Vaccine:

The RP-OspA and RP-OspC antigens were blended with stabilizer (sucrose, N-Z Amine, gelatin), 0.9% saline, amphotericin B, and gentamicin so that a 1.0 mL dose contained a target of $1.0\times10^8$ replicon particles/mL of each construct. The vaccine was then freeze dried.

Vaccination and Collection of Serum:

Dogs were vaccinated subcutaneously in the neck with a 1 mL dose of the combination vaccine and boosted with an additional 1 mL dose after 21 days. Whole blood was collected on study days 7, 14, 20, 29, 35, and 42 by venipuncture of the jugular vein. The serum was separated by centrifugation and stored at −10° C. or colder until tested.

Detection of Borreliacidal Antibodies:

OspA and OspC borreliacidal antibodies were detected using a flow cytometric procedure and *B. burgdorferi* ss S-1-10 or *B. burgdorferi* ss 50772, respectively [Canister et al., *Arch. Intern. Med.* 154:1625-1632 (1994)]. Detection of IgG antibodies: OspA and OspC antibodies were detected by ELISA.

Results

Vaccination with the combination vaccine reliably induced high levels of IgG and borreliacidal OspA and OspC antibodies at 2 weeks post-booster vaccination. The results demonstrate the ability of a combination vaccine comprising RP-OspA and RP-OspC to induce high levels of OspA and OspC borreliacidal antibodies and to induce high levels of RP-OspC opsonizing IgG antibodies.

Example 5

Combination Vaccine with RP-OspA and RP-OspC

Constructs:

The RP-OspA and RP-OspC constructs were produced as described above.

Animals:

Three month old beagles (Ridglan Farms) were housed communally in dog runs, and food and water was available ad libitum.

Preparation of the RP-OspA, and RP-OspC Combination Vaccine:

Treatment Group A received a combination of BEI inactivated bacterin of strains S-1-10 and 50772 (blended with 5% Emulsigen adjuvant solution-MVP Laboratories Inc., Omaha, US). The RP-OspA and RP-OspC antigens were blended with stabilizer (sucrose, N-Z Amine, gelatin), 0.9% saline, amphotericin B, and gentamicin so that a 1.0 mL dose contained a target of either 5.0×107 (Treatment Group B), 5.0×10⁶ (Treatment Group C), or 5.0×10⁵ (Treatment Group D) replicon particles/mL of each construct. The vaccines were freeze dried.

Vaccination and Injection Site Reactions:

Dogs were vaccinated subcutaneously in the neck with a 1 mL dose of the combination vaccine and boosted with an additional 1 mL dose after 21 days. Dogs were monitored for injection site reactions on study days 3 and 4 after the first vaccination and study days 24 and 25 after the second vaccination until no reaction could be felt (Table 4). The injection site reactions were evaluated based on type and size. Reactions were scored as visible, thickening, soft, hard, or tender, and reaction size was scored as S1=<1.0 cm, S2=1.0-2.0 cm, or S3=>2.0 cm.

Results

TABLE 4

| Injection site reactions | | | | | | | | |
|---|---|---|---|---|---|---|---|---|
| Treatment Group | Day 3 | Day 4 | Day 5 | Day 24 | Day 25 | Day 26 | Day 27 | Day 28 |
| A | S2 (T) | ○ | ○ | S1 (T) | S1 (S) | ○ | ○ | ○ |
| Whole Cell | S1 (T) | ○ | ○ | S1 (S) | S1 (S) | S1 (S) | S1 (H) | ○ |
| Bacterin | ○ | ○ | ○ | S1 (H) | S1 (H) | S1 (H) | ○ | ○ |
| Min. | S1 (S) | ○ | ○ | S1 (T) | ○ | ○ | ○ | ○ |
| Protective Dose | S1 (S) | ○ | ○ | S1 (S) | ○ | ○ | ○ | ○ |
| B | ○ | ○ | ○ | ○ | ○ | ○ | ○ | ○ |
| OspA, | ○ | ○ | ○ | ○ | ○ | ○ | ○ | ○ |
| OspC7, | ○ | S1 (S) | ○ | ○ | ○ | ○ | ○ | ○ |
| DbpA-tpA | ○ | ○ | ○ | ○ | ○ | ○ | ○ | ○ |
| $5.0 \times 10^7$ | ○ | ○ | ○ | ○ | ○ | ○ | ○ | ○ |
| C | ○ | ○ | ○ | ○ | ○ | ○ | ○ | ○ |
| OspA, | ○ | ○ | ○ | ○ | ○ | ○ | ○ | ○ |
| OspC7, | ○ | ○ | ○ | S2 (T) | ○ | ○ | ○ | ○ |
| DbpA-tPA | ○ | ○ | ○ | ○ | ○ | ○ | ○ | ○ |
| $5.0 \times 10^6$ | ○ | ○ | ○ | ○ | ○ | ○ | ○ | ○ |
| D | ○ | ○ | ○ | ○ | ○ | ○ | ○ | ○ |
| OspA, | ○ | ○ | ○ | ○ | ○ | ○ | ○ | ○ |
| OspC7, | ○ | ○ | ○ | ○ | ○ | ○ | ○ | ○ |
| Dbpa-tpA | ○ | ○ | ○ | ○ | ○ | ○ | ○ | ○ |
| $5.0 \times 10^5$ | ○ | ○ | ○ | ○ | ○ | ○ | ○ | ○ |

S1 = <1.0 cm;
S2 = 1.0-2.0 cm;
S3 = >2.0 cm;
T = thickening;
S = Soft;
H = Hard;
V = Visible
○ = no reaction

Example 6

Combination Vaccine with Dual Insert RP-OspA/C Constructs

Materials and Methods

Incorporation of the Coding Sequences for OspA and OspC, into the Alphavirus Replicon:

Ascl and Pacl digested TC-83-derived replicon vector "pVEK" was prepare as described in Example 1. Two DNA plasmids containing the codon-optimized open reading frame sequences of both the OspA and OspC, with 5' flanking sequence (5'-GGCGCGCCGCACC-3') [SEQ ID NO: 5] and 3' flanking sequence (5'-TTAATTAA-3'), were similarly digested with restriction enzymes Ascl and Pacl. The design of the synthetic gene cassettes incorporates one of the open reading frame sequences (OspA or OspC), a non-coding sequence containing the alphavirus subgenomic promoter and flanking sequences, and then the other desired open reading frame (OspA or OspC). The alphavirus subgenomic promoter and flanking sequences are 5'-GTT-TAAACTGTAAAACGACGGCCAGTAGTCGTCAT-AGCTGTTTCCTGGCTACCTGAGA GGGGCCCCTATAACTCTCTACGGCTAACCT-GAATGGACTACGACATAGTCTAGTCCGC CAAGA-TATCTTCAGCACCGGTGGCACC-3' [SEQ ID NO: 6]. This design duplicates a short portion of the 3' nsP4 open reading frame, the native alphavirus subgenomic promoter, and the 5' untranslated portion of the native subgenomic sequence. Also incorporated are restriction enzyme recognition sites, noncoding random sequences, primer binding sites, and a Kozak consensus sequence immediately 5' proximal to the second open reading frame. The synthetic gene cassettes were then ligated into the digested pVEK vector, and the resulting clones were re-named "pVDG-OspA-OspC" or "pVDG-OspC-OspA", with the order of the names denoting the relative 5' and 3' position within the cassette.

Production of RPs was conducted as described in Example 1.

Animals:

7-8 week old beagles (Ridglan Farms) were housed communally in dog runs, and food and water were available ad libitum.

Preparation of the RP-OspA/OspC or RP-OspC/OspA Vaccines:

The replicon RNA for each construct was electroporated in conjunction with helper RNAs (derived from VEE capsid helper and glycoprotein sequences) into Vero cells. Each replicon was packaged into RPs following the co-electroporation process generating the RP antigens. The resulting RPs were then collected in 0.4M NaCl phosphate buffer, formulated with 5% (w/v) sucrose, and quantified by immunofluorescence assay.

Three separate vaccines were blended with stabilizer (sucrose, N-Z Amine, gelatin) and 0.9% saline in a 1 mL dose. The vaccine in Treatment Group A contained a target dose of $5.0 \times 10^7$ for each separate RP-OspA and RP-OspC antigen. The vaccine in Treatment Group B contained a target dose of $5.0 \times 10^7$ for the RP-OspA/OspC dual construct antigen. The vaccine in Treatment Group C contained a target dose of $5.0 \times 10^7$ for the RP-OspC/OspA dual construct antigen. The vaccines were freeze-dried.

Vaccination and Collection of Serum:

Dogs were vaccinated subcutaneously in the neck with a 1 mL dose of the vaccine and boosted with an additional 1 mL dose after 21 days. Whole blood was collected on study days −1, 28, 35, 70, 92, and 119 by venipuncture of the jugular vein. The serum was separated by centrifugation and stored at −10° C. or colder until tested.

Detection of OspA and OspC Borreliacidal Antibodies:

OspA borreliacidal antibodies were detected using a flow cytometric procedure and *B. burgdorferi* ss S-1-10 [Callister et al., Arch. Intern. Med. 154:1625-1632 (1994)]. OspC borreliacidal antibodies were detected using a flow cytometric procedure and *B. burgdorferi* ss 50772 [Callister et al., Arch. Intern. Med. 154:1625-1632 (1994)].

Results

A vaccine containing separate RP-OspA and RP-OspC antigens induced moderate levels of borreliacidal antibodies at 1 week post-booster vaccination. At 1 week post-booster vaccination, a vaccine containing the RP-OspA/OspC dual construct antigen induced high levels of borreliacidal antibodies to OspC but relatively low levels of borreliacidal antibodies to OspA. In contrast, a vaccine containing the RP-OspC/OspA dual construct antigen induced high levels of borreliacidal antibodies to OspA, but relatively low levels of borreliacidal antibodies to OspC. The data suggest that a more robust borreliacidal antibody response to OspA or OspC was induced when that gene was in the downstream position of the construct (Table 5).

TABLE 5

Borreliacidal Data

| Treatment Group | OspA Borreliacidal Titers (Day 28) | OspC Borreliacidal Titers (Day 28) |
| --- | --- | --- |
| Treatment Group A | 5120 | 10240 |
| OspA + OspC | 2560 | 1280 |
| (Separate Constructs) | 10240 | 10240 |
|  | 2560 | 1280 |
|  | 320 | 5120 |
|  | 5120 | 5120 |
|  | 1280 | <80* |
| Geomean | 2560 | 2100 |
| Treatment Group B | 5120 | 20480 |
| OspA/OspC | 5120 | 20480 |
| (Dual Construct) | 80 | 20480 |
|  | 40 | 2560 |
|  | 320 | 20480 |
|  | 640 | 1280 |
|  | 5120 | 20480 |
| Geomean | 707 | 10240 |
| Treatment Group C | 5120 | <80* |
| OspC/OspA | 1280 | 80 |
| (Dual Construct) | 20480 | 2560 |
|  | 20480 | 10240 |
|  | 10240 | 80 |

TABLE 5-continued

Borreliacidal Data

| Treatment Group | OspA Borreliacidal Titers (Day 28) | OspC Borreliacidal Titers (Day 28) |
| --- | --- | --- |
|  | 2560 | 80 |
|  | 2560 | 640 |
| Geomean | 5653 | 320 |
| Treatment Group D | <80 | <80 |
| Placebo | <80 | <80 |
|  | <80 | <80 |
|  | <80 | <80 |
|  | <80 | <80 |
|  | <80 | <80 |
|  | <80 | <80 |
|  | <80 | <80 |
| Geomean | <80 | <80 |

*A value of 40 was used to determine the Geomean

Challenge with *B. burgdorferi* Infected *Ixodes scapularis* Ticks:

The experimental challenge with *B. burgdorferi*-infected ticks was conducted approximately 2 weeks after the second vaccination. Briefly, 9 female and 8 male adult ticks were placed onto the shaved side of each dog in a rubber cup that was held in place with tape and bandage wrap. The ticks were allowed to feed on the dogs for 7 days and removed. At 1, 2, and 3 months post-challenge, a skin biopsy was taken using a 4 mm puncture device from each dog, at a site adjacent to tick attachment site, for isolation of *B. burgdorferi*. The skin biospies were incubated in BSA rich media and observed for 4 weeks for the growth of *B. burgdorferi*. Tissue samples from the left side of the dog or from a limb that demonstrated limping and/or lameness were collected from the elbow, carpus, stifle, and tarsus and processed for isolation of *B. burgdorferi* by PCR (Table 6).

TABLE 6

Number of Dogs Positive for *B. burgdorferi* from Either the Skin or Joints

| Treatment Group | No. of Dogs Skin Biopsy Positive | No. of Dogs Joint Positive |
| --- | --- | --- |
| Treatment Group A: | 0/7 | 0/7 |
| OspA + OspC |  |  |
| (Separate Constructs) |  |  |
| Treatment Group B: | 0/7 | 0/7 |
| OspA/OspC |  |  |
| (Dual Construct) |  |  |
| Treatment Group C: | 0/7 | 0/7 |
| OspC/OspA |  |  |
| (Dual Construct) |  |  |
| Treatment Group D: | 6/7 | 5/7 |
| Placebo |  |  |

SEQUENCE TABLE

| SEQ ID NO: | Description | Type |
|---|---|---|
| 1 | Outer Surface Protein A | nucleic acid |
| 2 | Outer Surface Protein A | amino acid |
| 3 | Outer Surface Protein C | nucleic acid |
| 4 | Outer Surface Protein C | amino acid |
| 5 | ggcgcgccgcacc | nucleic acid |
| 6 | GTTTAAACTGTAAAACGACGGCCAGTAGTCGTCATAGCTGTTTCCTGGCTACCTGAGAGGGGCCCCTATAACTCTCTACGGCTAACCTGAATGGACTACGACATAGTCTAGTCCGCCAAGATATCTTCAGCACCGGTGGCACC | nucleic acid |

SEQUENCES

Outer Surface Protein A (SEQ ID NO: 1)
atgaaaaagtaccttttgggaatcggactcattctcgccctgatcgcctgcaagcaaaacgtgtcct
ccctcgacgaaaagaactcagtgtcggtggatctgcccggcgaaatgaaggtgctcgtgtccaaga
gaagaacaaggatggaaaatacgacctgattgccaccgtggacaagctggagttgaagggcacctca
gacaagaacaacgggtctggagtgctggaaggagtcaaagcggacaagtccaaggtcaagctgacta
tttcggacgacctgggccagactaccctggaagtgttcaaggaggacggaaagaccctggtgtccaa
gaaggtcacctccaaggataagtcgagcaccgaagagaagttcaatgagaagggagaagtgtcggag
aagatcatcacccgcgccgatggaacccggctggagtacaccgagatcaagtccgatggttcggga
aaggctaaggaagtcctgaagggctacgtgcttgagggtactctgactgcggaaaagaccactctggt
ggtcaaggaaggcaccgtgactctgtcaaagaacatctccaagagcggagaagtcagcgtggaactg
aacgacacagattcctccgctgccacgaaaaagaccgccgcctggaacagcgggaccagcactctca
ccattaccgtgaacagcaaaaagactaaggacctggtgttcaccaaggagaacacgatcaccgtgca
gcagtatgactccaacggtaccaagctcgaagggtccgccgtggagatcactaagctggacgagatt
aagaatgcactgaagtga Outer Surface Protein A (SEQ ID NO: 2)
MKKYLLGIGLILALIACKQNVSSLDEKNSVSVDLPGEMKVLVSKEKNKDG
KYDLIATVDKLELKGTSDKNNGSGVLEGVKADKSKVKLTISDDLGQTTLE
VPFKEDGKTLVSKKVTSKDKSSTEEKFNEKGEVSEKIITRADGTRLEYTEI
KSDGSGKAKEVLKGYVLEGTLTAEKTTLVVKEGTVTLSKNISKSGEVSVE
LNDTDSSAATKKTAAWNSGTSTLTITVNSKKTKDLVFTKENTITVQQYDS
NGTKLEGSAVEITKLDEIKNALK*

Outer Surface Protein C SEQ ID NO: 3
atgaagaagaatactctctccgccattctgatgaccctgttcctgttttatctcctgcaacaactccg
ggaaggatggcaacacctcggccaactccgccgatgaaagcgtcaagggtcccaacctgactgagat
ctcgaagaaaatcaccgagtccaacgcggtggtgttggcagtgaaggaggtcgaaactctgctgact
agcatcgacgagcttgccaaggccattggaaagaagattaagaacgacgtgtcactggacaacgaag
ctgaccataacggatctcttatctcgggcgcttacctgatttcgaccctcatcaccaagaagatctc
cgcgatcaaggacagcggggagctcaaggccgaaattgagaaagcaaagaagtgctccgaagagttc
accgcgaagctcaagggagaacacaccgacctgggaaaggaaggcgtcaccgatgataacgcgaaga
aggccatcctcaaaaccaacaacgacaagacaaagggcgccgacgaactggagaagctgttcgagag
cgtgaagaatctgtccaaggccgccaaggaaatgttgacgaacagcgtgaaggaactgacctcccct
gtggtggccgagtcaccgaaaaagccatga Outer Surface Protein C (SEQ ID NO: 4)
MKKNTLSAILMTLFLFISCNNSGKDGNTSANSADESVKGPNLTEISKKIT
ESNAVVLAVKEVETLLTSIDELAKAIGKKIKNDVSLDNEADHNGSLISGA
YLISTLITKKISAIKDSGELKAEIEKAKKCSEEFTAKLKGEHTDLGKEGV
TDDNAKKAILKTNNDKTKGADELEKLFESVKNLSKAAKEMLTNSVKELTS
PVVAESPKKP*

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. An immunogenic composition comprising two or more alphavirus RNA replicon particles each individually encoding one or more *Borrelia burgdorferi* antigens;

wherein one alphavirus RNA replicon particle encodes a *Borrelia burgdorferi* outer surface protein A (OspA), wherein the OspA consists of the amino acid sequence of SEQ ID NO: 2, and wherein another alphavirus RNA replicon particle encodes a *Borrelia burgdorferi* outer surface protein C (OspC), wherein the OspC consists of the amino acid sequence of SEQ ID NO: 4; wherein both OspA-borreliacidal and OspC-borreliacidal antibodies are induced in a canine when said canine is immunized with said immunogenic composition.

2. A vaccine to aid in the prevention of disease due to *Borrelia burgdorferi* infection comprising the immunogenic composition of claim 1, and a pharmaceutically acceptable carrier.

3. An immunogenic composition comprising an alphavirus RNA replicon particle that encodes two or more *Borrelia burgdorferi* antigens; wherein at least one *Borrelia burgdorferi* antigen is an outer surface protein A (OspA) and wherein at least one other *Borrelia burgdorferi* antigen is an outer surface protein C (OspC), wherein at least one OspA comprises the amino acid sequence of SEQ ID NO: 2, and at least one OspC, comprises the amino acid sequence of SEQ ID NO: 4; and wherein both OspA-borreliacidal and OspC-borreliacidal antibodies are induced in a canine when said canine is immunized with said immunogenic composition.

4. The immunogenic composition of claim 3 comprising a first and a second alphavirus RNA replicon particle each individually encoding an OspA and an OspC wherein the first RNA replicon particle comprises a nucleic acid sequence encoding OspA that is located upstream of a nucleic acid sequence encoding OspC, and the second RNA replicon particle comprises a nucleic acid sequence encoding OspC that is located upstream of a nucleic acid sequence encoding OspA.

5. The immunogenic composition of claim 3, wherein at least one of the alphavirus RNA replicon particles is a Venezuelan Equine Encephalitis Virus (VEEV) RNA replicon particle.

6. The immunogenic composition of claim 5, that comprises one or more additional alphavirus RNA replicon particles which encode a *Borrelia burgdorferi* antigen selected from the group consisting of a second OspA that originates from a different strain of *Borrelia burgdorferi* than the OspA, a second OspC that originates from a different strain of *Borrelia burgdorferi* than the OspC, and any combination thereof.

7. The immunogenic composition of claim 6, wherein the one or more additional alphavirus RNA replicon particles are VEEV RNA replicon particles.

8. The immunogenic composition of claim 5, wherein at least one OspA consists of the amino acid sequence of SEQ ID NO: 2 and at least one OspC consists of the amino acid sequence of SEQ ID NO: 4.

9. A vaccine to aid in the prevention of disease due to *Borrelia burgdorferi* infection comprising the immunogenic composition of claim 5 and a pharmaceutically acceptable carrier.

10. The vaccine composition of claim 9, further comprising at least one non-*Borrelia* immunogen for eliciting protective immunity to a non-*Borrelia* pathogen.

11. The vaccine of claim 10, wherein the non-*Borrelia* immunogen is a killed or attenuated non-*Borrelia* pathogen selected from the group of killed or attenuated non-*Borrelia* pathogens consisting of canine distemper virus, canine adenovirus, canine parvovirus, canine parainfluenza virus, canine coronavirus, canine influenza virus, Leptospira serovars, *Leishmania* organisms, *Bordetella bronchiseptica*, *Mycoplasma* species, rabies virus, *Ehrlichia canis*, an *Anaplasma* species, and any combination thereof.

12. The vaccine of claim 11, wherein the *Mycoplasma* species comprises *Mycoplasma cynos*.

13. The vaccine of claim 12, wherein the Leptospira serovars are selected from the group consisting of *Leptospira kirschneri* serovar grippotyphosa, *Leptospira interrogans* serovar canicola, *Leptospira interrogans* serovar icterohaemorrhagiae, *Leptospira interrogans* serovar pomona, and any combination thereof.

14. The vaccine composition of claim 9, further comprising an alphavirus RNA replicon particle comprising a nucleotide sequence encoding at least one protein antigen or an antigenic fragment thereof from a non-*Borrelia* immunogen.

15. The vaccine of claim 14, wherein the non-*Borrelia* immunogen comes from a non-*Borrelia* pathogen selected from the group consisting of canine distemper virus, canine adenovirus, canine parvovirus, canine parainfluenza virus, canine coronavirus, canine influenza virus, Leptospira serovars, *Leishmania* organisms, *Bordetella bronchiseptica*, *Mycoplasma* species, rabies virus, *Ehrlichia canis*, an *Anaplasma* species, and any combination thereof.

16. The vaccine composition of claim 9, that is a nonadjuvanted vaccine.

17. A method of immunizing a mammal against a pathogenic *Borrelia* genospecies comprising administering to the mammal an immunologically effective amount of the vaccine of claim 9, 10, 14, 15, 11, 12, 13 or 16.

* * * * *